United States Patent [19]

Gambale

[11] Patent Number: 5,569,258
[45] Date of Patent: Oct. 29, 1996

[54] LAMINECTOMY RONGEURS

[75] Inventor: Charles E. Gambale, East Boston, Mass.

[73] Assignee: Logan Instruments, Inc., East Boston, Mass.

[21] Appl. No.: 493,763

[22] Filed: Jun. 22, 1995

[51] Int. Cl.6 .................................................. A61B 17/00
[52] U.S. Cl. ........................... 606/83; 606/167; 606/170; 606/171
[58] Field of Search .................................... 606/167, 170, 606/171, 205, 206, 207, 83, 185, 79, 82, 184, 190, 107

[56] References Cited

U.S. PATENT DOCUMENTS 5,273,519 12/1993 Koros et al. ............................ 606/171
5,385,570 1/1995 Chin et al. ............................ 606/170
5,451,227 9/1995 Michaelson ............................ 606/170

OTHER PUBLICATIONS

Neurosurgical Instrument Calalog, Ruggles Corporation, 1969.
Kerrison Rounjuer Drawings, No date, pp. 1–3.
Commerical Product, of Logan Instrument. Made in 1992.

Primary Examiner—Michael Powell Buiz
Assistant Examiner—Kevin Truong
Attorney, Agent, or Firm—Wolf, Greenfield & Sacks, P.C.

[57] ABSTRACT

A laminectomy rongeur with top and bottom parallel bars in sliding relation, one to the other, with the ends cooperating to form cutting tips. The lower bar has an upwardly longitudinally extending flange and an orthogonally related reinforcing wall extending laterally of the upwardly extending flange. An ejecting flange integral with and longitudinal of the longitudinally extending flange projects beyond the cutting tip of the top bar when the ends forming the cutting tips are spread apart.

5 Claims, 3 Drawing Sheets

LAMINECTOMY RONGEURS

SUBJECT MATTER OF THE INVENTION

The present invention relates to improved laminectomy rongeurs.

BACKGROUND MATTER OF INVENTION

Laminectomy rongeurs are used by neurosurgeons and orthopedic surgeons for cutting disks or other spinal bone structures. In general, these instruments are designed to clamp and sever small segments of bone structure in a nibbling or biting-like procedure. Thus, in performing these cutting tasks, surgeons frequently encounter difficult sections which require the wiggling or twisting of the instruments. This movement places a great deal of strain on these rongeurs which frequently damages them. In conventionally styled rongeurs, the damage often involves the snapping of the lower bar near its tip. Additionally, the rongeur edges frequently roll over and are dulled even if the tip does not fracture the cutting edges as a result of forces applied from the twisting and wiggling movement.

The fracturing of the tip and the dulling of the edges in these conventional rongeurs is a direct result of the particular construction of the rongeurs heretofore used. These constructions are such that the two bars or jaws that are the major components of forming the rongeurs are often secured together by a double pivot which causes non-parallel movement of the bars during use. In addition, the inherent weakness of conventional rongeurs is also partially due to the mechanism of the upper and lower bars that permits one bar to slide relative to the other as well as to construction at the cutting tip of the instrument.

Cutting fragments, bones, soft tissue, and ligamentum fiavum are often caught in the cutting edge of the upper bar forming the rongeurs. This debris must be removed prior to another use of the rongeurs. Frequently, the surgeon uses a second rongeurs while the first is being cleaned of debris in the cutting edge by a nurse.

SUMMARY OF INVENTION

It is an object of this invention to provide improved laminectomy rongeurs which are less likely to break or have cutting edges that become dull when in use than has been possible heretofore with prior art constructions.

It is also an object of the present invention to provide improved laminectomy rongeurs which are not likely to break near the cutting tip during use. A further object of the present invention is to provide an improved laminectomy rongeur design which may be adapted for use with rongeurs of a variety of sizes.

One further object of the present invention is to provide an improved laminectomy rongeur utilizing upper and lower bars that slide parallel to one another, rather than in a non-parallel relationship.

A further object of the present invention is to provide an improved laminectomy rougeur in which a single pivot is used in conjunction with an actuating lever to slide the upper bar relative to the lower bar. One further object of this invention is to provide an improved construction at the cutting tip which minimizes the likelihood that the bars will crack when twisted and subjected to unusual strain or forces.

One further object of the present invention is to provide an improved laminectomy rongeur with means for removing debris, such as cutting fragments, bones, soft tissue, and ligamentum flavum, from the cutting tip of the instrument as the instrument is in use. This object of the present invention further contemplates a laminectomy rongeur which may be used by a surgeon during an operation without the need to discontinue use of the rongeurs while it is being cleaned by an assistant.

In the present invention the laminectomy rongeur is formed with an upper and lower bar having means for securing the bars together for relative parallel sliding movement in a direction along their lengths. The cutting tip of the rongeur is formed by interlocking the cutting with means that define a laterally extending reinforcing element along substantially the entire length of the rongeur. In a further feature of the invention the upper and lower bars are locked together with means provided to effect parallel movement of the upper bar with respect to the lower bar.

DETAILED DESCRIPTION OF INVENTION

These and other advantages of the present invention will be more clearly understood when considered in conjunction with the accompanying drawings in which.

DETAILED DESCRIPTION OF REFERRED EMBODIMENT

Figure 1:
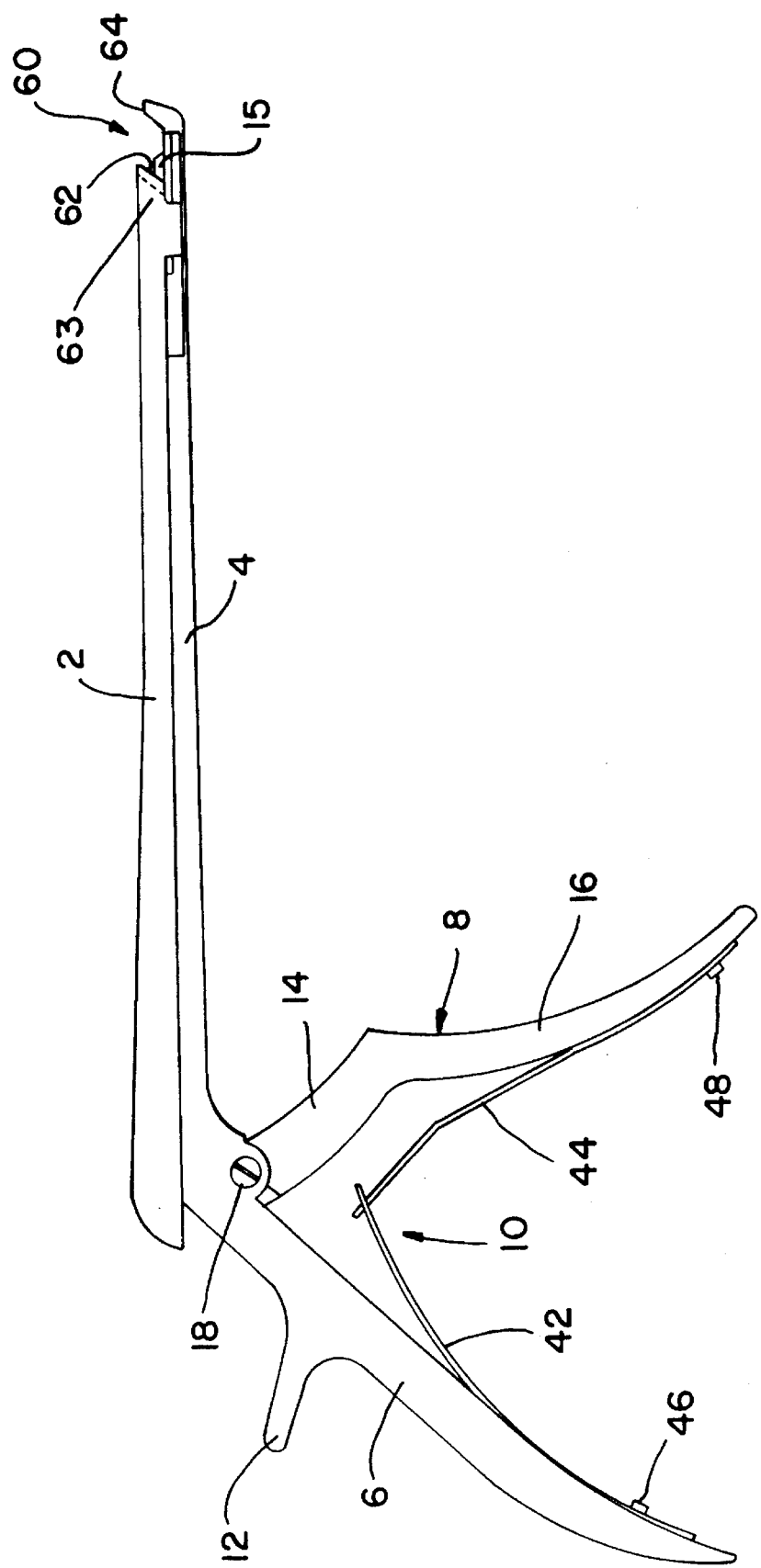
FIG. 1 is a plan elevational view of a laminectomy rongeur embodying the present invention.

The laminectomy rongeur of the present invention comprises a top or upper bar 2 and a bottom or lower bar 4 with an integrally formed handle 6 and an actuator or actuating lever 8 pivotally connected to the handle 6. The actuator lever 8 is spring loaded in a normal open position by spring assembly 10.

The handle 6 and grasping portion of actuator lever 8 may be consistent with existing laminectomy rongeur designs. In such arrangements, the handle 6 is conveniently formed with a shape that fits the hand and provides essentially a pistol grip engagement. A stop 12 extending rearwardly from the handle 6 is shaped to engage the operator's hand just above the thumb and forefinger. The actuator lever 8 may be shaped with a upper leg 14 and lower leg 16, with a lower leg 16 angularly curved to be conveniently engaged by the users forefingers. The upper leg 14, extending angularly from the lower leg 16, is pivotally secured by pivot pin 18 to the upper end of the handle 6. The upper end of the leg 14 extends through a slot 20 (FIG. 2) at the upper end of the handle 6 and terminates at end 22. An actuator lever slot 23 is formed in end 22. The actuator lever 8 is pivotally secure to the handle in slot 20 by the pin 18. This pin 18 extends through the walls of the handle 6 that form the slot 20 and through a hole in the leg 14 which is sandwiched between these facing walls.

Figure 2:
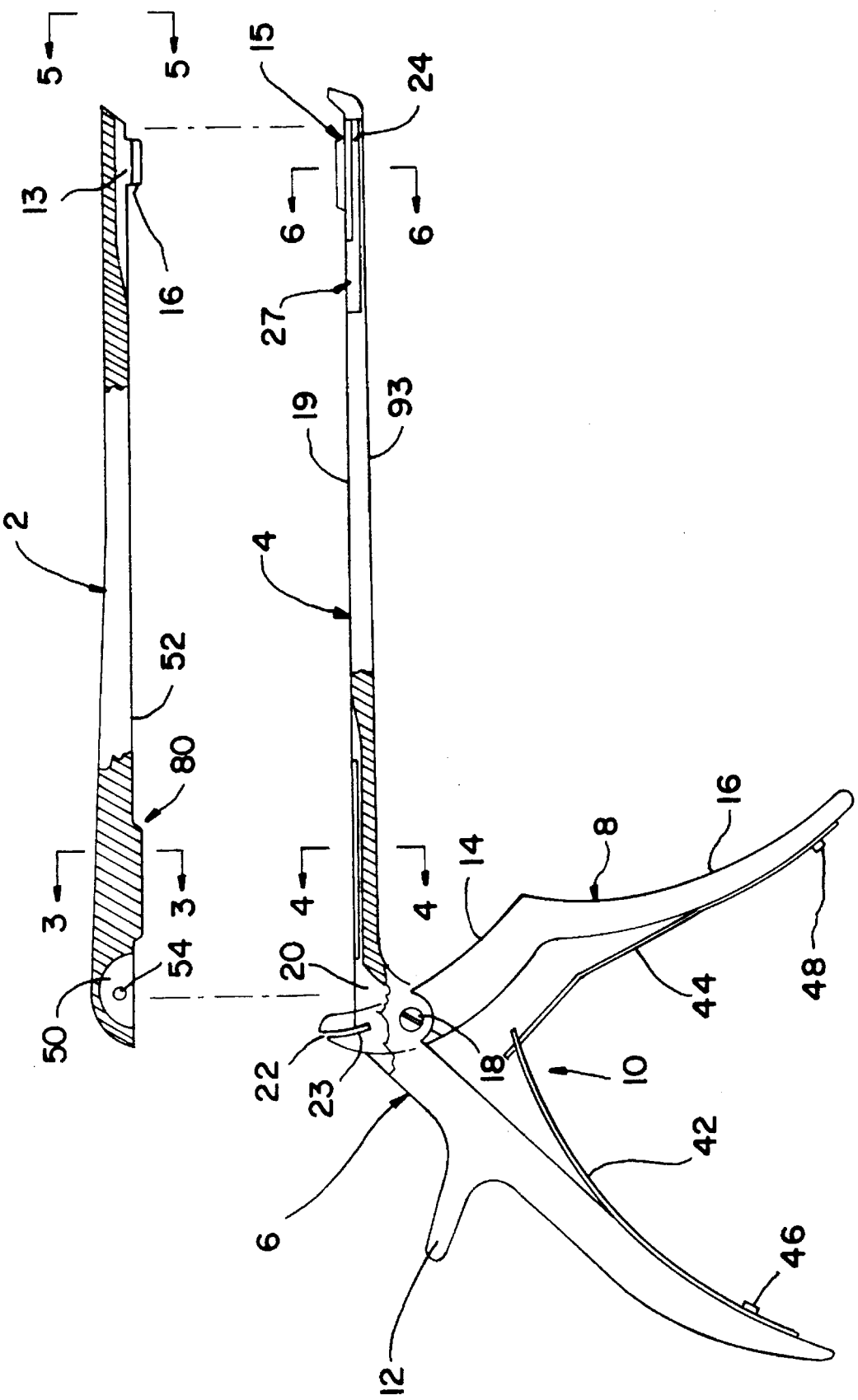
FIG. 2 is a partially exploded plan elevational view of the embodiment of FIG. 1, illustrating the upper and bottom bars in partial cross section.

The actuator lever 8 is normally spring loaded in an open position as illustrated in FIG. 1 and 2 by the leaf spring assembly 10 which comprises leaf springs 42 and 44. Each of these leaf springs, 42 and 44 is secured at its lower end to the lower ends respectively of the handle 6 and actuator lever 8 by screws 46 and 48. The leaf springs 42 and 44 are interengaged at their upper ends by a tongue in leaf spring 44 and groove in leaf spring 42. By properly shaping these leaf springs 42 and 44 as illustrated, the actuator lever 8 will normally be spring loaded away from the handle 6 as illustrated in FIG. 2 unless a compressing force is affirmatively applied to the hand gripping instrument.

The top bar 2 is positioned in facing relation above the bottom bar 4 as illustrated in FIG. 1, with the top bar 2 adapted to slide longitudinally along the upper wall of the bottom bar when the actuator lever 8 is closed against the spring tension of the spring assembly 10. This sliding movement is, in part, achieved by the interengagement of the top or upper bar 2 with the upper end of leg 14. The upper end of leg 14 is positioned in a slot 50 which extends lengthwise in the bottom wall 52 of upper bar 2. A pin 54 extends from one side wall of the upper bar 2 through slot 23 in the end 22 to the other side wall that defines the slot 50.

The upper or top bar 2 has an elongated relatively flat and narrow shape that flares from the cutting tip 60 of limited height to the other end.

The cutting elements of cutting tip 60 as illustrated in FIG. 1 may be conventional in design. In such a design, aligned cutting edges 62 and 64 are formed on aligned portions of the top and bottom bars respectively. The cutting edge 62 may have a conventional inverted U-shape (FIG. 5) and the cutting edge 64 of the lower bar 4 may have a complementary shaped cutting surface.

The cutting edges 62 and 64 are preferably aligned with one another and are angular with respect to the length of the upper and lower bars 2 and 4 as illustrated in FIGS. 1 and 2.

The cutting edge 62 in the end of bar 2 is defined by forming within its edge a concave recess 63 shown in dotted outline in FIG. 1 in the end wall of the upper bar 2. The concave recess is conventionally used to receive soft tissue, bone segments, and debris as they are cut or nipped from the spinal structure. This debris ordinarily adheres to the concave recess 63 (FIG. 1 ) in the upper bar 2, as the bar is withdrawn. The debris is removed in the manner discussed below.

The cutting tip 60 of the top bar 2 is also formed with a channel 13 (FIGS. 2 and 5) extending rearwardly from the end of the cutting tip toward the handle 6. This channel 13 may vary in dimension, but is preferably centrally located with respect to the side walls of the top bar 2 and extends upwardly from its lower wall 52 about ½ the height of the bar. The channel 13 extends rearwardly a sufficient distance to accommodate sliding movement of debris ejecting flange 15 (FIG. 2) that extends upwardly from the top wall 19 of the bottom bar 4. This flange 15 ejects debris caught in the concave recess 63 of the top of bar 2 when the actuator lever 8 is released. As best illustrated in FIG. 1, the ejector flange 15 projects beyond the cutting edge 62 when the actuator arm 8 is in a released position. However, when the actuator arm 8 is closed and the cutting edges 62 and 64 are close to one another in cutting relationship, the edge 62 has been moved beyond the end of ejector flange 15. As the actuator arm 8 is released and the bar 2 moves rearwardly with respect to bar 4, the edge 62 slides over the end of flange 15. This causes debris caught in the concave recess 63 to be engaged by the end of flange 15 and thereby be ejected from the rongeurs as the bar 2 continues to move rearwardly.

Figure 5:
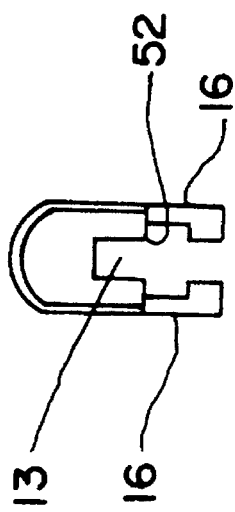
FIG. 5 is a cross sectional view taken along the line of 5—5 of FIG. 2.

Extending downwardly from the facing sidewalls of the top bar 2 are a pair of flanges 16 which terminate in inwardly extending lips (FIG. 5). The flanges 16 slide along a reduced thickness of the lower bar 4 at the cutting tip 60 end. These flanges 16 and lips are also spaced apart and are shaped to engage longitudinally extending channels 24 and 25 respectively in the sidewalls 27 and 28 at the forward end of the bottom bar 4. This interengagement of the lips and channels locks the top and bottom bars together in sliding relation at the forward end.

Figure 3:
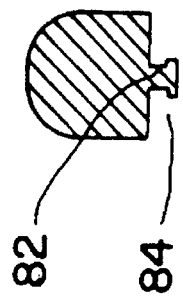
FIG. 3 is a cross sectional view taken along the line of 3—3 of FIG. 2.
Figure 4:
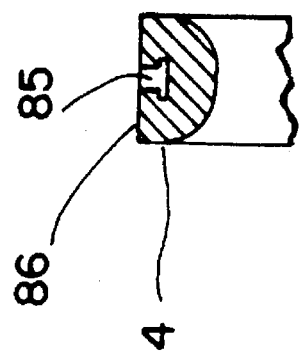
FIG. 4 is a cross sectional view taken along the line of 4—4 of FIG. 2.

The top bar 2 and bottom bar 4 are also slidingly interengaged at the rear end by a tongue and groove arrangement 80 as shown best in FIGS. 2, 3, and 4. The tongue and groove arrangement at the rear end include a downwardly extending flange 82 with outwardly extending lips 84 lengthwise on either side to form a inverted T-shaped member. A correspondingly shaped channel 85 is formed in the upper wall 86 of the bottom bar 4. The downwardly extending T-shape member slides longitudinally within the channel 85 when the upper bar 2 slides longitudinally of the lower bar 4.

Figure 6:
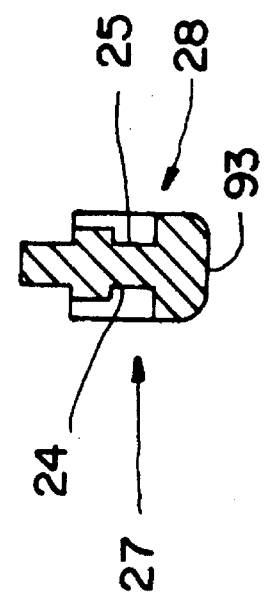
FIG. 6 is a cross sectional view taken along the line of 6—6 of FIG. 2.

The reduced thickness of the cutting tip end and the channels 24 and 25 effectively narrow the lower bar 2 along the length of the cutting tip as to form an elongated flange illustrated in FIG. 6. However the bottom wall 93 of the lower bar 4 has the same width at the cutting tip as does the rear end of bar 4. This full thickness of wall 93 at the cutting tip provides a reinforcing member of about three times the thickness of the otherwise narrowed cutting tip end, that extends the length of the lower bar 4 that is orthogonally related to the elongated flange formed at the cutting tip end. This reinforcing member thus forms an inverted T-shaped bar which effectively reinforces the cutting tip.

What is claimed is:

1. A laminectomy rongeur having a top bar and a bottom bar having adjacent ends forming a cutting tip, means securing said bars together in parallel adjacent relation, means for longitudinally sliding one bar relative to the other said lower bar having a cross section along at least the cutting tip end which includes an upwardly longitudinally extending flange, and an orthogonally related reinforcing wall that extends laterally beyond said longitudinally extending flange and an ejecting flange integral with and extending longitudinally of said longitudinally extending flange with said ejecting flange projecting beyond said cutting tips of said top bar when said cutting tips are spread apart.

2. A laminectomy rongeur as set forth in claim 1 wherein said cutting tip is formed of a pair of aligned cutting edges with one each extending from corresponding ends of said upper and lower bars, said ejecting flange beng shorter than said longitudinally exending flange means forming longitudinally extending channels in said longitudinally extending flange, and a pair of flanges extending downwardly from said upper bar and terminating in inwardly extending legs that engage said channels.

3. A laminectomy rongeur as set forth in claim 2 wherein said means for longitudinally sliding one bar relative to the other comprises of a lever arrangement having a single pivot.

4. A laminectomy rongeur having a top bar and a bottom bar having adjacent ends forming a cutting tip, means securing said bars together in parallel adjacent relation, means for longitudinally sliding one bar relative to the other, and means connected to one of said bars for ejecting debris that is caught on the cutting tip as the bars are moving one relative to the others.

5. A laminectomy rongeur as set forth in claim 4, wherein said means for ejecting comprises an elongated flange secured to one of said bars and adapted to move longitudinally with respect to at least one of the cutting edges formed at said cutting tip.

\* \* \* \* \*